United States Patent [19]

Hovis

[11] Patent Number: 5,146,036
[45] Date of Patent: Sep. 8, 1992

[54] TRANSFER OF CATALYST

[75] Inventor: Keith W. Hovis, Bartlesville, Okla.

[73] Assignee: Phillips Petroleum Company, Bartlesville, Okla.

[21] Appl. No.: 648,301

[22] Filed: Jan. 22, 1991

Related U.S. Application Data

[62] Division of Ser. No. 464,263, Jan. 12, 1990, Pat. No. 5,021,223.

[51] Int. Cl.$^5$ .............................................. C07C 2/58
[52] U.S. Cl. ...................................... 585/723; 585/709
[58] Field of Search ............................... 585/723, 709

[56] References Cited

U.S. PATENT DOCUMENTS

| | | | |
|---|---|---|---|
| 2,488,943 | 11/1949 | Shearer | 585/723 |
| 2,615,928 | 10/1952 | Jolly | 585/723 |
| 3,080,438 | 3/1963 | Sailors | 585/723 |
| 3,249,650 | 5/1966 | Fenske | 260/683.48 |
| 3,953,538 | 4/1976 | Boney | 585/723 |
| 4,409,420 | 10/1983 | Van Pool et al. | 585/723 |

OTHER PUBLICATIONS

*Hydrofluoric Acid Alkylation*, Phillips Petroleum Company Publication, pp. 31-31, and 35-36 and FIG. 15., 1946.

*Primary Examiner*—Anthony McFarlane
*Assistant Examiner*—Nhat Phan
*Attorney, Agent, or Firm*—Charles W. Stewart

[57] ABSTRACT

An improved system for performing an alkylation process and a method for handling liquid catalyst in an alkylation process. This improvement involves method and apparatus by which liquid alkylation catalyst contained in the alkylation process equipment can be transferred into a catalyst storage vessel without the need for venting excess pressure from the storage vessel to atmosphere. Through a combination of the physical arrangement of the process equipment and the storage vessel along with the addition of a pressure equalization line, apparatus is provided whereby certain process steps can be followed which allow the transfer of catalyst from the process equipment to the storage vessel without venting the storage vessel. The improvement comprises physically locating the catalyst storage vessel at a relative elevation below the alkylation proces equipment and providing a line to connect the vapor space of the storage vessel with that of a catalyst settling vessel in the process equipment.

4 Claims, 1 Drawing Sheet

TRANSFER OF CATALYST

This application is a Division of application Ser. No. 464,263, filed Jan. 12, 1990, now U.S. Pat. No. 5,021,223.

This invention relates to an improved method and an improved apparatus for handling fluids. It further relates to an apparatus and method for handling fluids in an alkylation process.

A common process used in the petroleum refining industry is an alkylation process where high octane gasoline is produced by reacting, in the presence of catalyst, preferably hydrogen fluoride, isoparaffins with olefin compounds. One commonly used version of this alkylation process is similar to that disclosed in U.S. Pat. No. 3,213,157 which uses a settling vessel, reactor riser, and a cooler heat exchanger that are combined in a manner which allow for the natural circulation of liquid alkylation catalyst. A hydrocarbon feed mixture of isoparaffins and olefins is introduced into the inlet of a reactor riser at which point cooled alkylation catalyst exiting from a heat exchanger is intimately mixed with the hydrocarbon feed thereby forming a hydrocarbon-catalyst mixture. Due to the density difference between the hydrocarbon-catalyst mixture and catalyst, the mixture flows upwardly by natural convection through the reactor riser with the reactor effluent ultimately discharging into a settler vessel. In the settler vessel, separation of the non-miscible hydrocarbon phase from the catalyst phase takes place with the catalyst phase settling to the lower portion of the vessel to form a liquid-liquid interface between the hydrocarbon and catalyst. The settled-out catalyst returns by gravity to the heat exchanger located somewhere below the settler where it is cooled and again mixed with incoming hydrocarbon feed to repeat the cycle. The operating conditions of such an alkylation process are well known in the art and have been disclosed in many various publications and, for example, in U.S. Pat. No. 3,213,157, No. 3,249,650, and No. 3,544,651.

A concern associated with the operation of an alkylation process is the safe handling, transportation, and storage of alkylation catalyst. As is typically provided, a storage vessel is used to inventory any make-up catalyst which may be needed to periodically recharge the process as catalyst is consumed during its operation; but, also, the storage vessel is used to store, when required, the inventory of catalyst contained in the process. This inventory of catalyst is primarily, but not exclusively, contained in the settler vessel, reactor riser, heat exchanger, and the interconnecting piping. As often happens, non-condensable gases enter the catalyst storage vessel by various means such as the pressurization system used to transfer fresh catalyst from plant receiving and unloading facilities to the storage vessel. Due to the presence of these non-condensable gases in the storage vessel, any attempts to transfer the inventory of catalyst contained in the process without resort to venting of the vessel to atmosphere or flare via a treating system is prevented. This is due to the pressurization of the catalyst storage vessel by the non-condensable gases as the catalyst from the process is being transferred. The pressurization of the storage vessel results in the elimination of the pressure driving force needed to continue said catalyst transfer.

A typical alkylation unit provides means for venting to atmosphere or flare, via a treating system, the catalyst storage vessel during a catalyst transfer either from the process or from receiving and unloading facilities; however, because of environmental and economic considerations, this is an undesirable procedure. An additional problem which is encountered while transferring catalyst from the process to the storage vessel is that, in cases where the process pressure is equal to that in the storage vessel, there is no motive force to drive the catalyst into the vessel thus leaving behind in the process piping and vessels catalyst which is unable to gravitate into the storage vessel.

It is an object of this invention to provide improved method and means for handling catalyst fluids in an alkylation process.

An additional object of this invention is to provide means by which the inventory of liquid catalyst within the process system of an alkylation unit can, be transferred into a storage vessel by use of gravitational force without resort to venting such vessel to atmosphere or flare.

Further objectives of this invention are to improve the environmental safety in operating an alkylation unit, to improve the economics of operating an alkylation unit by minimizing catalyst consumption, and to provide a quick method for transferring catalyst into a safe haven storage vessel.

SUMMARY OF THE INVENTION

The objects of this invention are broadly accomplished by an arrangement of equipment connected together in such a manner as to allow the transfer of alkylation catalyst from process vessels, equipment, and interconnecting piping to a catalyst storage vessel without the need for venting said storage vessel during the transfer.

In one embodiment of this invention, the catalyst storage vessel is positioned in a location having a relative elevation below such process equipment as, for example, the heat exchanger for cooling catalyst, the settler vessel, the reactor riser and all interconnecting piping. Also included in this embodiment is a vent line which connects the vapor space of the storage vessel and the vapor space of the settler vessel so as to allow the equalization of pressure between the two vessels during draining of catalyst to storage. Under this embodiment, the contents of the storage vessel are isolated from the process by installing two remotely operated valves one of which is located in the line connecting the storage vessel with the process at an elevation point above the storage vessel but below the process equipment and piping, and the other remotely operated valve being located in the vent line connecting the process settling vessel and the catalyst storage vessel. With this invention, the catalyst draining operation can be conducted without, as previously done, venting process pressure from the catalyst storage vessel to the atmosphere via a neutralization system and flare.

Other aspects, objects, and advantages of this invention will become apparent from the study of this disclosure, appended claims, and the drawing that is provided for illustrating an embodiment of this invention.

DETAILED DESCRIPTION OF THE INVENTION

Figure 1:
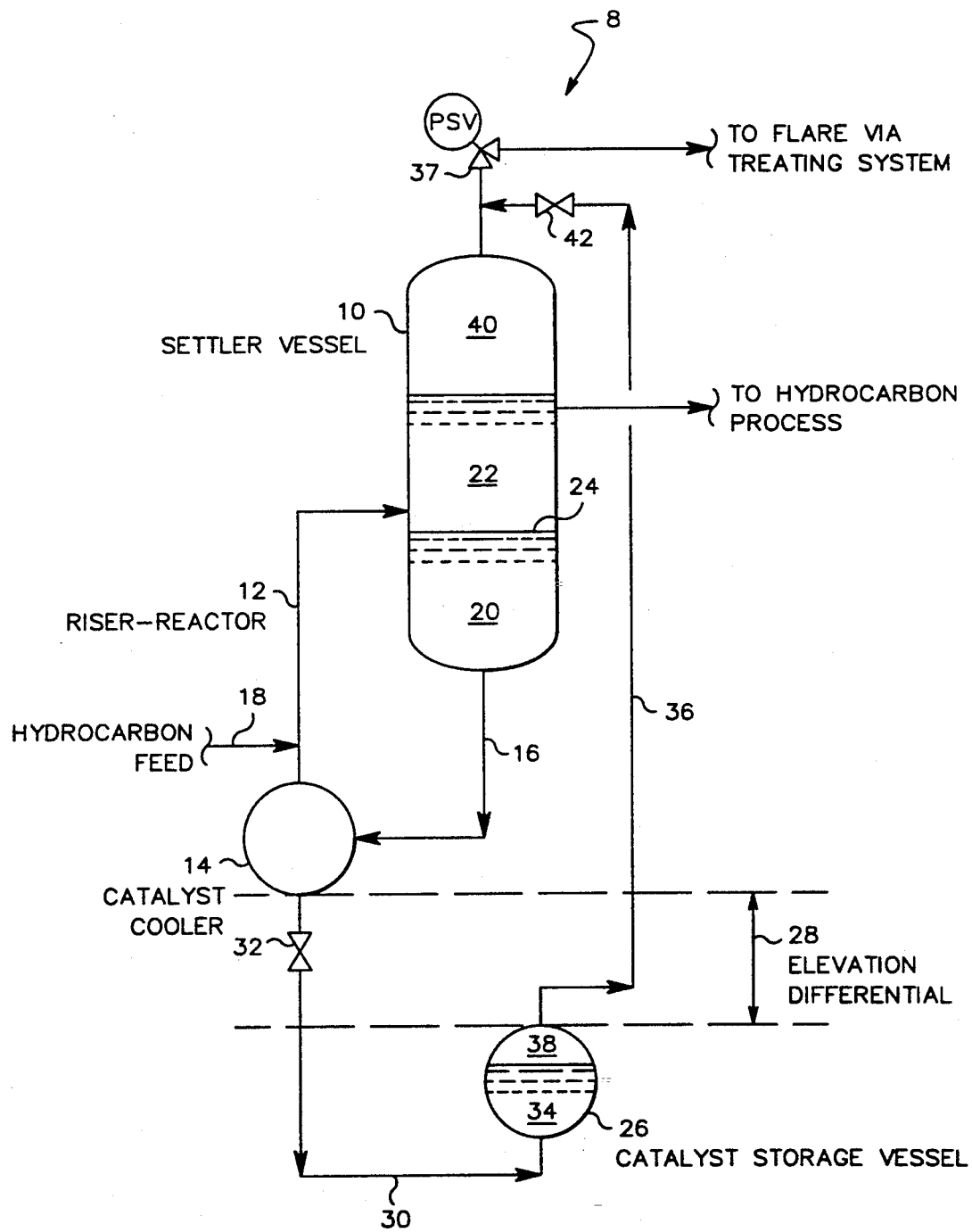
FIG. 1 is a simplified schematic representation of the portion of an alkylation process comprising an alkylation reactor riser, settler, cooler heat exchanger, and storage vessel illustrating such an arrangement suitable for carrying out the invention.

Referring to FIG. 1, there is illustrated a catalytic alkylation apparatus and process. Because the carrying out of this invention is not dependent upon the specific alkylation process operating conditions, such as reaction temperature, reactor pressure, catalyst-to-hydrocarbon mixture ratios, and isoparaffin-to-olefin mixture ratios and because these operating conditions are well known in the art, they are not discussed in this description.

Shown in FIG. 1 is system 8 for performing an alkylation process which comprises settler vessel 10, riser-reactor 12, catalyst cooler 14 and conduit 16 in fluid flow communication between the lower portion of the settler vessel 10 and the catalyst cooler 14. Hydrocarbon feed material comprising a mixture of olefins and isoparaffins is introduced through conduit 18 into the lower portion of the riser-reactor 12 which is in fluid flow communication between the catalyst cooler 14 and the medial portion of the settler vessel 10. The hydrocarbon feed material is introduced at essentially the outlet of the catalyst cooler 14 where circulating liquid catalyst flows by natural convection from settler vessel 10 via conduit 16 through catalyst cooler 14 and mixes with the injected hydrocarbons from conduit 18 to form an admixture. A presently preferred liquid catalyst for use in the system of the present invention comprises a mixture of HF acid and water. The thus formed admixture rises upwardly through riser-reactor 12 where the reactor effluent discharges from riser-reactor 12 into settler vessel 10. Upon entering settler vessel 10, two separate liquid phases form with the catalyst phase 20 settling to the lower portion of settler vessel 10 and with the hydrocarbon phase 22 forming above the catalyst phase and with a liquid-liquid interface 24 being formed therebetween. The catalyst circulates continuously through the system by settling out in settler vessel 10 and passing through conduit 16, catalyst cooler 14, and riser-reactor 12.

In order to provide a safe, reliable and rapid method for transfering alkylation catalyst from the alkylation process equipment without using the catalyst storage standard approach of pressuring settler vessel 10 while simultaneously venting vessel 26 during the transfer operation, catalyst storage vessel 26 is positioned at a relative elevation below those elevations of the alkylation process equipment comprising settler vessel 10, riser-reactor 12, catalyst cooler 14, and conduit 16. In one embodiment, the catalyst storage vessel 26 can be positioned below ground level. This elevation differential is shown at 28. Conduit 30 provides fluid flow communication between the lower portion of catalyst cooler 14 and the lower portion of catalyst storage vessel 26. During the draining operation, a remotely operated valve 32, which is interposed in conduit 30, at a relative elevation above catalyst storage vessel 26 but below said process equipment comprising settler vessel 10, riser-reactor 12, catalyst cooler 14, and conduit 16, is opened to allow draining of catalyst by way of conduit 30. As the catalyst is draining, the level of catalyst phase 34 in storage vessel 26 rises and the level of catalyst phase 20 in settler vessel 10 falls.

Vent line 36 interconnects the upper portion of the catalyst storage vessel 26 and the upper portion of the settler vessel 10 to serve as a conduit providing fluid flow communication between vapor space 38 of catalyst storage vessel 26 and vapor space 40 of settler vessel 10. Vapor Space 40 of settler vessel 10 is isolated from the downstream treating and flare systems (not shown) by pressure safety valve 37. The pressure between vessels 10 and 26 is equalized by the opening of a remotely operated valve 42 interposed in vent line 36, which valve 42 is also used to isolate the vapor spaces of vessels 10 and 26 when valve 42 is in its closed position. The opening of valve 42 during the draining operation results in the equalization of vapor space pressure of the two vessels and thus allows the draining of catalyst from said process equipment to catalyst storage vessel 26 by the exclusive use of gravitational motive force.

EXAMPLE

The following calculated example is presented to illustrate the application of the invention on a commercial scale. Table I shows the existing conditions in the acid settler vessel along with the appurtenant equipment, and it shows the conditions in the catalyst storage vessel. The initial conditions indicated in Table I show the volume of catalyst in each of the vessels, the initial vapor space pressures in each vessel, and the relative liquid catalyst elevation in each vessel. Further shown are the changes in conditions in each of the vessels as the invention is operated.

TABLE I

|  | Initial | Final (W/O Venting) | Final (With Venting) |
|---|---|---|---|
| Quantity of acid catalyst in settler 10, riser-reactor 12, cooler 14, and piping | 400,000 lb | 150,000 lb | 0 |
| Pressure in vapor space 40 of settler 10 | 120 psia | 110 psia | 111 psia |
| Level of acid catalyst 20 in settler 10 and conduits connecting catalyst storage vessel 26 relative to level of acid catalyst 34 in storage vessel 26 | 30 ft | 10 ft | −10 ft |
| Quantity of acid catalyst 34 | 50,000 lb | 300,000 lb | 450,000 lb |
| Pressure in vapor space 38 of storage vessel 26 | 60 psia | 115 psia | 111 psia |

Initially, before beginning the operation of draining catalyst from the process equipment, there is generally a pressure differential between the vapor space 40 of settler vessel 10 and vapor space 38 of storage vessel 26. As the catalyst is drained from settler vessel 10, the liquid level elevation differential between the two vessels changes and the non-condensable gases present in vapor space 38 of storage vessel 26 are compressed. This process continues until the pressure between the two vessels equalizes and, in the case where the storage vessel 26 elevation is below that of settler vessel 10, the pressure in vapor space 38 of storage vessel 26 will rise to a point which exceeds the pressure in the settler vessel 10 by the amount of the elevation head of the liquids in settler vessel 10. This results in equalizing the energy potentials at the liquid levels of the respective vessels 10 and 26. The vent line 36, which connects the vapor spaces of the storage vessel 26 and settler vessel 10, provides a conduit for the equalization of the pressure in the vapor spaces of the two vessels. With an open vent line 36, the elevation head of the catalyst remaining in the process equipment is further utilized to drain the remaining catalyst into storage vessel 26 and thereby complete the draining operation.

Reasonable variations and modifications may be made in the combination and arrangement of parts or elements or in the processes as heretofore set forth in the specification and shown in the drawing without departing from the spirit and scope of the invention as defined in the following claims.

That which is claimed is:

1. A method of performing an alkylation reaction including settling an admixture of a liquid hydrocarbon and a liquid catalyst in a settler vessel to separate said liquid hydrocarbon from said liquid catalyst; cooling the thus separated liquid catalyst; mixing the thus cooled separated liquid catalyst with a hydrocarbon feed to produce a mixture thereof; reacting the thus produced mixture of the cooled separated liquid catalyst and the hydrocarbon feed; and circulating the thus reacted mixture of liquid catalyst and hydrocarbon feed to said settler vessel, the improvement comprising:

providing first conduit means connected in fluid flow communication between said settler vessel and a storage vessel for transferring the separated liquid catalyst to said storage vessel with said first conduit means having interposed therein, at a relative elevation above said storage vessel and below said settler vessel, first valve means for blocking passage of fluid through said first conduit means and, alternatively, for allowing passage of fluid through said first conduit means;

opening said first valve means to thereby transfer the separated liquid catalyst via said first conduit means from said settler vessel to said storage vessel by gravitational means;

providing second conduit means connected in fluid flow communication between said storage vessel and said settler vessel for venting the vapor space of said storage vessel to the vapor space of said settler vessel and having interposed therein, at a relative elevation above said storage vessel, second valve means for blocking passage of fluid therethrough and, alternatively, for allowing passage of fluid through said second conduit means; and opening said second valve means to thereby equalize the pressure between the vapor space of said storage vessel and the vapor space of said settler vessel to thereby allow for further draining of said separated liquid catalyst via first conduit means from said settler vessel to said storage vessel by gravitational means.

2. A method as recited in claim 1, further comprising:
closing said first valve means and said second valve means to thereby store and isolate said separated liquid catalyst within said storage vessel.

3. A method as recited in claim 2 wherein:
said storage vessel is positioned below ground level.

4. A method as recited in claim 3 wherein:
the liquid catalyst comprises a mixture of HF acid and water.

* * * * *